United States Patent

Büchel et al.

[11] 3,993,765
[45] Nov. 23, 1976

[54] 1-PROPYL-TRIAZOLYL ANTIMYCOTIC COMPOSITIONS AND METHODS OF TREATING MYCOSES

[75] Inventors: Karl Heinz Büchel; Wolfgang Krämer; Manfred Plempel, all of Wuppertal, Germany

[73] Assignee: Bayer Aktiengesellschaft, Germany

[22] Filed: Sept. 23, 1974

[21] Appl. No.: 508,684

[30] Foreign Application Priority Data
Oct. 5, 1973  Germany............................ 2350121

[52] U.S. Cl. .................................................. 424/269
[51] Int. Cl.[2] ........................................ A61K 31/41
[58] Field of Search ................................... 424/269

[56] References Cited
UNITED STATES PATENTS
3,812,142   5/1974   Buchel et al. ........................ 424/269

*Primary Examiner*—Jerome D. Goldberg

[57] ABSTRACT

Pharmaceutical compositions are produced which comprise an antimycotically effective amount of a compound of the formula

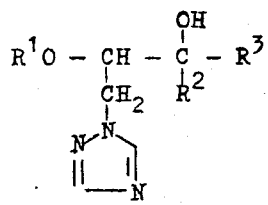

or a pharmaceutically acceptable non-toxic salt thereof wherein
$R^1$ is an unsubstituted or substituted aryl moiety,
$R^2$ is hydrogen, alkyl, alkenyl, cycloalkyl, unsubstituted or substituted aryl or unsubstituted or substituted aralkyl, and
$R^3$ is hydrogen, alkyl or cycloalkyl,
provided that when $R^3$ is hydrogen, $R^2$ cannot be hydrogen, in combination with a pharmaceutically acceptable nontoxic inert diluent or carrier.

43 Claims, No Drawings

1-PROPYL-TRIAZOLYL ANTIMYCOTIC COMPOSITIONS AND METHODS OF TREATING MYCOSES

The present invention is concerned with pharmaceutical compositions useful for treating mycoses in humans and animals, as well as to methods of treating mycoses in humans and animals. The active compounds of the present compositions and the active agents used in the method according to the present invention are 1-propyl-triazolyl compounds.

More particularly, the present invention is concerned with pharmaceutical compositions useful for treating mycoses in humans and animals which comprises an antimycotically effective amount of a compound of the formula

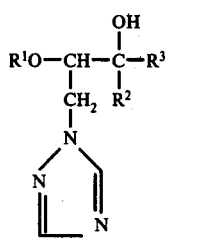

or a pharmaceutically acceptable non-toxic salt thereof wherein
- $R^1$ is an aryl moiety, especially aryl of 6 to 10 carbon atoms, and particularly phenyl or naphthyl, unsubstituted or substituted by 1 or more, preferably 1 to 3, and especially 1 or 2, of the same or different substituents selected from the group consisting of alkyl of 1 to 4 carbon atoms, halogen, haloalkyl of 1 or 2 carbon atoms in the alkyl moiety and 2 to 5 halogen moieties, alkoxy, especially alkoxy of 1 to 4 carbon atoms, haloalkoxy, especially of 1 to 4 carbon atoms in the alkoxy moiety and 3 to 5 halogen moieties, alkylthio, especially of 1 to 4 carbon atoms in the alkyl moiety, haloalkylthio, especially of 1 to 4 carbon atoms in the alkyl moiety and 3 to 5 halo moieties, alkylsulphonyl, especially of 1 to 4 carbon atoms in the alkyl moiety, nitro, amino, and phenyl;
- $R^2$ is hydrogen; alkyl of 1 to 6 carbon atoms, especially of 1 to 4 carbon atoms; alkenyl of 2 to 6 carbon atoms; cycloalkyl of 5 to 7 carbon atoms, an aryl moiety, especially of 6 to 10 carbon atoms, particularly phenyl or naphthyl, unsubstituted or substituted by 1 or more, especially 1 to 3, and particularly 1 or 2, of the same or different substituents selected from the group consisting of alkyl of 1 to 4 carbon atoms, halogen, alkoxy, especially alkoxy of 1 to 4 carbon atoms, haloalkoxy, especially of 1 to 4 carbon atoms in the alkoxy moiety and 3 to 5 halogen moieties, alkylthio, especially of 1 to 4 carbon atoms in the alkyl moiety, haloalkylthio, especially of 1 to 4 carbon atoms in the alkyl moiety and 3 to 5 hao moieties, alkylsulphonyl, especially of 1 to 4 carbon atoms in the alkyl moiety, nitro, amino and phenyl; or an aralkyl moiety, especially of 6 to 10 carbon atoms in the aryl moiety and of 1 or 2 carbon atoms in the alkyl moiety, particularly benzyl, unsubstituted or substituted by 1 or more, especially 1 to 3, and particularly 1 or 2, of the same or different substituents selected from the group consisting of alkyl of 1 to 4 carbon atoms, halogen, alkoxy, especially alkoxy of 1 to 4 carbon atoms, haloalkoxy, especially of 1 to 4 carbon atoms in the alkoxy moiety and 3 to 5 halogen moieties, alkylthio, especially of 1 to 4 carbon atoms in the alkyl moiety, haloalkylthio, especially of 1 to 4 carbon atoms in the alkyl moiety and 3 to 5 halo moieties, alkylsulphonyl, especially of 1 to 4 carbon atoms in the alkyl moiety, nitro, amino and phenyl; and
- $R^3$ is hydrogen, alkyl of 1 to 6 carbon atoms, especially of 1 to 4 carbon atoms, or cycloalkyl of 5 to 7 carbon atoms, especially 5 or 6 carbon atoms;
provided that when $R^3$ is hydrogen, $R^2$ cannot be hydrogen.

When $R^2$ and/or $R^3$ is alkyl, the alkyl moieties include straight- as well as branched-chain alkyl moieties.

The following alkyl moieties are representative of those for $R^2$ and $R^3$: methyl, ethyl, n-propyl, i-propyl, n-butyl, i-butyl and t-butyl. A particularly preferred alkyl moiety for $R^2$ is methyl; and a particularly preferred alkyl moiety for $R^3$ is t-butyl.

When $R^3$ is cycloalkyl, cyclohexyl and cyclopentyl are preferred.

When $R^2$ is a substituted aryl or aralkyl moiety, the preferred substituents include straight- or branched-chain alkyl moieties of 1 to 4 carbon atoms, for example, methyl, ethyl, n-propyl, i-propyl, n-butyl, i-butyl and t-butyl, halogen, especially fluorine or chlorine, alkoxy, particularly of 1 or 2 carbon atoms such as methoxy and ethoxy, haloalkoxy such as trifluoromethoxy and pentafluoroethoxy, and haloalkylthio such as trifluoromethylthio, as well as nitro, amino and o- and p-phenyl.

When $R^1$ is substituted aryl, the preferred substituents include straight- or branched-chain alkyl of 1 to 4 carbon atoms such as methyl, ethyl, n-propyl, i-propyl, n-butyl, i-butyl or t-butyl, halogen, especially fluorine, chlorine and bromine, haloalkyl, especially wherein the halogen is fluorine and/or chlorine, for example, trifluoromethyl, haloalkoxy such as those wherein the halogen is fluorine and/or chlorine, such as trifluoromethoxy, difluorochloromethoxy and pentafluoroethoxy, alkoxy of 1 or 2 carbon atoms such as methoxy or ethoxy, haloalkylthio such as trifluoromethylthio or chlorodifluoromethylthio, as well as nitro, amino and o- and p-phenyl, or carbalkoxy of 1 to 4 carbon atoms in the alkoxy portion.

According to one embodiment of the present invention
- $R^1$ is phenyl, naphthyl or phenyl substituted by 1 to 3 substituents selected from the group consisting of fluorine, chlorine, bromine, methyl, tert.-butyl, and phenyl;
- $R^2$ is hydrogen, alkyl of 1 to 4 carbon atoms, cycloalkyl of 5 or 6 carbon atoms, phenyl, naphthyl or benzyl; and
- $R^3$ is hydrogen, alkyl of 1 to 4 carbon atoms or cycloalkyl of 5 or 6 carbon atoms; provided that when $R^3$ is hydrogen, $R^2$ cannot be hydrogen.

According to another embodiment of the present invention
- $R^1$ is phenyl unsubstituted or substituted by 1 or 2 substituents selected from the group consisting of chlorine, fluorine, bromine or methyl;
- $R^2$ is hydrogen or alkyl of 1 to 4 carbon atoms; and
- $R^3$ is alkyl of 1 to 4 carbon atoms.

According to another embodiment of the present invention $R^1$ is phenyl, chlorophenyl especially m-chlorophenyl or p-chlorophenyl, dichlorophenyl especially 2,4-dichlorophenyl, fluorophenyl, especially p-fluorophenyl, bromophenyl especially p-bromophenyl, or chloromethylphenyl especially 4-chloro-2-methylphenyl;

$R^2$ is hydrogen, methyl or t.-butyl; and $R^3$ is t.-butyl.

According to another embodiment of the present invention $R^1$ is 4-chlorophenyl or 4-fluorophenyl;

$R^2$ is hydrogen or methyl; and $R^3$ is t.-butyl; the hydrochloride salt thereof or the nitrate thereof.

According to another embodiment of the present invention $R^1$ is phenyl unsubstituted or substituted by 1 or 2 members selected from the group consisting of chlorine, fluorine and methyl;

$R^2$ is hydrogen, methyl, cyclohexyl or benzyl; and $R^3$ is hydrogen or t.-butyl; provided that when $R^3$ is hydrogen, $R^2$ cannot be hydrogen.

According to another embodiment of the present invention $R^1$ is phenyl, chlorophenyl, dichlorophenyl, fluorophenyl, dimethylphenyl or chloromethylphenyl;

$R^2$ is hydrogen, methyl, phenyl, chlorophenyl, or benzyl; and $R^3$ is hydrogen or t.-butyl; provided that when $R^3$ is hydrogen, $R^2$ cannot be hydrogen.

The 1-propyl-triazolyl active compounds of the present invention are obtainable both in the erythro form and in the threo form. These forms can be separated by fractional crystallization or via their tartrates. However, the active compounds are predominantly in racemic form.

The erythro form and the threo form can be separated into their optical antipodes in accordance with techniques per se known. The present invention includes use of the active compounds in the form of optical isomers as well as racemates.

The pharmaceutically acceptable non-toxic salts of the above-referred-to compounds include salts formed with such acids as the hydrogen halide acids, phosphoric acid, nitric acid, monofunctional and bifunctional carboxylic acids, hydroxycarboxylic acids, for example, acetic, maleic acid, succinic acid, fumaric acid, tartaric acid, citric acid, salicylic acid, sorbic acid and lactic acid, and 1,5-naphthalenedisulphonic acid. The hydrochlorides and nitrates are preferred salts.

Representative 1-propyl-triazolyls according to the above invention include:

1-(1,2,4-triazol-1-yl)-2-(4-chlorophenoxy)-3-hydroxy-4,4-dimethylpentane, 1-(1,2,4-triazol-1-yl)-2-(3-chlorophenoxy)-3-hydroxy-4,4-dimethylpentane, 1-(1,2,4-triazol-1-yl)-2-(2,4-dichlorophenoxy)-3-hydroxy-4,4-dimethylpentane, 1-(1,2,4-triazol-1-yl)-2-(4-fluorophenoxy)-3-hydroxy-4,4-dimethylpentane, 1-(1,2,4-triazol-1-yl)-2-phenoxy-3-hydroxy-4,4-dimethylpentane, 1-(1,2,4-triazol-1-yl)-2-(4-chlorophenoxy)-3-hydroxy-3,4,4-trimethylpentane, 1-(1,2,4-triazol-1-yl)-2-(2-chlorophenoxy)-3-hydroxy-4,4-dimethylpentane, 1-(1,2,4-triazol-1-yl)-2-(4-chlorophenoxy)-3-hydroxy-3-benzyl-4,4-dimethylpentane, 1-(1,2,4-triazol-1-yl)-2-(2-methyl-4-chlorophenoxy)-3-hydroxy-4,4-dimethylpentane, and 1-(1,2,4-triazol-1-yl)-2-(4-chlorophenoxy)-3-cyclohexyl-3-hydroxypropane.

The 1-propyl-triazoles of formula (I) may be prepared by reducing 1-ethyl-triazoles of the formula $$R^1O-CH-\underset{\underset{\underset{N}{|}}{\underset{CH_2}{|}}}{\overset{\overset{O}{\|}}{C}}-R^3 \quad (II)$$

(triazole ring)

wherein $R^1$ and $R^2$ are as above defined, in accordance with techniques per se known, either with or without the simultaneous introduction of the $R^2$ moiety.

The reduction of the triazoles II can be carried out (a) with hydrogen in the presence of a catalyst (for example, Raney nickel) and a polar solvent (for example, methanol) at a temperature of from 20° C to 50° C or, (b) with aluminum isopropylate in the presence of an inert solvent at a temperature of from 20° C to 120° C followed by hydrolysis, or (c) with a complex hydride (for example, sodium borohydride) in the presence of a polar solvent (for example, methanol) at a temperature or from 0° C to 30° C, followed by a hydrolysis (for example, with aqueous hydrochloric acid), or (d) with formamidinesulphinic acid and an alkali metal hydroxide (for example, sodium hydroxide) in aqueous solution at a temperature of from 20° C to about 100° C in the presence of a polar solvent (for example, ethanol).

The 1-propyl-triazoles of formula (I) can also be prepared by (e) subjecting compounds of formula II to reductive alkylation, cycloalkylation, aralkylation or arylation by means of Grignard reagents such as alkyl-, cycloalkyl-, aralkyl- or aryl-magnesium halides (preferably, iodides or bromides; for example, with methylmagnesium iodide) in anhydrous diethyl ether at a temperature of from 20° C to 80° C and subsequent hydrolysis, for example, with aqueous ammonium chloride solution. The compounds of the present invention thus obtained can be isolated in accordance with customary methods and, if desired, purified, for example, by distilling off any solvent, extracting the mixture with water and organic solvents, for example, ethyl acetate or methylene chloride, drying the organic phase and freeing it from the solvent. The residue thereby obtained can be further purified by recrystallization or salt formation.

The 1-propyl-triazoles of formula I and their salts can be interconverted in any of the ways customary for the interconversion of free organic bases and their salts. For example, the base may be converted into a salt by dissolving the base in an ether (for example, diethyl ether) and adding the acid (for example, hydrogen chloride). The salt can be isolated in a known manner, for example, by filtration, and purified, if desired.

The triazoles of formula II can be prepared according to German Patent Application P 23 35 020.1 corresponding to the U.S. application Ser. No. 483,758, filed 27. 6. 1974 [Le A 1500] by: (a) reacting a compound of the formula

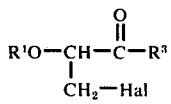 (III)

wherein $R^1$ and $R^3$ are as above defined, and

Hal is halogen, preferably chlorine or bromine, with 1,2,4-triazole, either in the presence or in the absence of a polar solvent, and of an acid-binding agent, at a temperature of from 50° C to 100° C. Compounds of formula II can be isolated and purified in the usual manner.

Compounds of formula III are not known but can be prepared according to techniques per se known. For example, they can be obtained when phenols or naphthols of the formula $$R^1OH \qquad (IV),$$

wherein $R^1$ is as above defined, are condensed with haloketons of the formula $$Hal-CH_2-CO-R^3 \qquad (V),$$

wherein $R^3$ is as above defined, and

Hal is halogen, preferably chlorine or bromine, in a manner per se known, and the resulting ketone of the formula $$R^1O-CH_2-CO-R^3 \qquad (VI),$$

wherein $R^1$ and $R^3$ are as above defined, is reacted in accordance with techniques per se known in the presence of alkali (such as aqueous sodium hydroxide solution with formaldehyde or a formaldehyde donor such as a 40% strength aqueous formaldehyde solution) in an inert solvent (such as ethanol) at an elevated temperature (for example, at the boiling point of the reaction mixture) and the desired product is isolated and purified in the manner per se known. Alternatively, the resulting hydroxymethyl compound of the formula

 (VII)

wherein $R^1$ and $R^3$ are as above defined, is subsequently treated without isolation with a halogenating agent (such as thionyl chloride) in an inert polar solvent (such as methylene chloride) at room temperature. The isolation and purification of the compounds of formula III can be carried out in accordance methods per se known (for example, those set forth in Example 1).

The active compounds of the present invention are useful for their antimicrobial and, particularly, their strong antimycotic effects. They have a broad antimycotic spectrum of activity, especially against dermatophytes and blastomyces, as well as biphase fungi, for example, against species of Candida (such as *Candida albicans*), species of Epidermophyton (such as *Epidermophyton floccosum*), species of Aspergillus (such as *Aspergillus niger*), species of Trichophyton (such as *Trichophyton mentagrophytes*), species of Microsporon (such as *Microsporon felineum*) and species of Penicillium (such as *Penicillium commune*), as well as biphase fungi such as Histoplasma, Coccidiodes and Sporotrichum. The list of these microorganisms in no way represents a limitation of the microbes which can be combated and is only illustrative in character.

The following may be mentioned as examples of fields of indication in human medicine: dermatomycoses and systemic mycoses caused by *Trichophyton mentagrophytes* and other species of Trichophyton, species of Microsporon, *Epidermophyton floccosum*, blastomyces and biphase fungi as well as molds.

The following may be mentioned as examples of fields of indication in veterinary medicine: all dermatomycoses and systemic mycoses, especially those caused by the above-mentioned pathogens.

The good microbiological activity of the active compounds of the invention is demonstrated by the following in vitro and in vivo experiments.

1. Determination of the antimycotic activity in vitro (series dilution test).

Description of the experiment:

The nutrient substrate used was Sabourauds' milieu d'epreuve. The incubation temperature was 28° C and the incubation time was 24 to 96 hours. The test pathogens employed were *Candida albicans* and *Trichophyton mentagrophytes* as well as *Penicillin commune, Aspergillus niger* and *Microsporon felineum, Cocciodiodes, immitis, Torulopsis glabrata* and other less important pathogens.

Table A shows at what concentration growth was no longer detectable (MIC).

Table A

Minimum inhibitory concentration in γ/ml of nutrient medium.

| Active compound | Trichophyton mentagrophytes | Candida albicans | Penicillium commune |
|---|---|---|---|
| 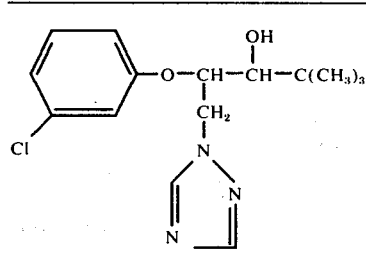 | >64 | >64 | >64 |

Table A-continued

Minimum inhibitory concentration in γ/ml of nutrient medium.

| Active compound | Trichophyton mentagrophytes | Candida albicans | Penicillium commune |
| --- | --- | --- | --- |
| [2-chlorophenoxy derivative] | 32 | 32+ | >64 |
| [2,4-dichlorophenoxy derivative] | 4 | 8+ | >64 |
| [2,5-dichlorophenoxy derivative] | 32 | 64+ | >64 |
| [2,3-dimethylphenoxy derivative] | 64* | 64 | 64 |
| [4-fluorophenoxy derivative] | 64 | 64+ | 64 |

+50% action
*90% action

2. Antimycotic action of the compounds of the invention, in animal experiments.

a. Action, on oral administration, against Quinckeanum trichophytosis of white mice.

By using doses of 100 mg/kg of body weight, administered orally twice daily up to the eighth day of the infection, it was possible to suppress the development of the Quinckeanum infection in mice.

The result can be seen in Table B.

Table B

Action of the compounds of the invention in Quinckeanum trichophytosis of white mice:

| Compound from Example No. | Action against Trichophyton Quinckeanum (orally administered) |
| --- | --- |
| 4 | ++ |

Legend
++weak action, that is, fewer than 30% of the animals show infection symptoms.

b. Candidosis of mice

Description of the experiment

Mice of type $SPF\text{-}CF_1$ were infected intravenously with $1\text{-}2 \times 10^6$ of logarithmically growing Candida cells which were suspended in physiological sodium chloride solution. One hour before and seven hours after the infection, the animals were treated orally, in each case with 100 mg of the preparations/kg of body weight.

Untreated animals died of the infection 3 to 6 days after the infection. The survival rate on the 6th day after infection was about 5% in the case of untreated control animals.

The experimental results are summarized in Table C.

Table C

| Action in candidosis of mice Compound from Example No. | Action in candidosis of mice |
|---|---|
| 4 | ++++ |
| 7 | ++++ |

Legend
++++good action = 80% survivors on the 6th day after infection.

The pharmaceutical compositions of the present invention contain a major or minor amount, e.g. 0.1 to 99.5%, preferably 0.5 to 95% of active ingredient as above defined in combination with a pharmaceutically acceptable non-toxic inert diluent or carrier, the carrier comprising one or more solid, semi-solid or liquid diluent, filler and formulation adjuvant which is non-toxic, inert and pharmaceutically acceptable. Such pharmaceutical compositions are preferably in dosage unit form; i.e., physically discrete units containing a predetermined amount of the drug corresponding to a fraction or multiple of the dose which is calculated to produce the desired therapeutic response. The dosage units can contain one, two, three, four or more single doses or, alternatively, one half, third or fourth of a single dose. A single dose preferably contains an amount sufficient to produce the desired therapeutic effect upon administration at one application of one or more dosage units according to a predetermined dosage regimen, usually a whole, half, third or quarter of the daily dosage administered once, twice, three or four times a day. Other therapeutic agents can also be present.

Although the dosage and dosage regimen must in each case be carefully adjusted, utilizing sound professional judgment considering the age, weight and condition of the recipient, the route of administration and the nature and gravity of the illness, generally the dosage will be 10 mg/kg to 300 mg/kg, preferably from 50 mg/kg to 200 mg/kg, of body weight per day. In some instances a sufficient therapeutic effect can be obtained at a lower dose, while in others, a larger dose will be required.

Oral administration can be effected utilizing solid and liquid dosage unit forms such as powders, tablets, dragees, capsules, granulates, suspensions, solutions and the like.

Powders are prepared by comminuting the compound to a suitable fine size and mixing with a similarly comminuted pharmaceutical carrier such as an edible carbohydrate as for example starch, lactose, sucrose, glucose or mannitol. Sweetening, flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated for example by preparing a powder mixture, granulating or slugging, adding a lubricant and disintegrant and pressing into tablets. A powder mixture is prepared by mixing the compound, suitably comminuted, with a diluent or base as described above, and optionally with a binder such as carboxymethyl cellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous sucrose solution while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxyethylene sorbitol esters, preservatives, flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a non-toxic liquid vehicle suitable for injection such as an aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administration. Non-toxic salts and salt solutions can be added to render the injection isotonic.

Stabilizers, preservatives and emulsifiers can also be added.

Rectal administration can be effected utilizing suppositories in which the compound is admixed with low-melting water-soluble or insoluble solids such as polyethylene glycol, cocoa butter, higher esters as for example myristyl palmitate, or mixtures thereof.

Topical administration can be effected utilizing solid dosage unit forms such as powders or liquid or semiliquid dosage unit forms such as solutions, suspensions, ointments, pastes, creams and gels. The powders are formulated utilizing such carriers as talc, bentonite, silicic acid, polyamide powder and the like. Liquid and semi-liquid formulations can utilize such carriers, in addition to those described above, as polyethylene glycol, vegetable and mineral oils, alcohols such as isopropanol and the like. Other excipients such as emulsifiers, preservatives, colorants, perfumes and the like can also be present. Formulations can also be administered as an aerosol, utilizing the usual propellants such as the chlorofluorohydrocarbons.

The preferred daily dose is 0.5g to 30 g, especially 2.5 g to 20 g, of active agent.

While the routes of administration include oral, parenteral (i.e., intramuscular, intraperitoneal, and intravenous), rectal, and topical, oral administration and topical application are particularly preferred.

The preferred pharmaceutical compositions are therefore those in a form suitable for oral administration such as tablets and suspensions and those suitable for topical application such as ointments.

The following Examples A to D describe by way of illustration only the preparation of pharmaceutical compositions and a medicament in dosage unit form according to the present invention.

Example A: 1% strength solution for topical application:

Sufficient polyethylene glycol 400 is added to 1 g of the compound from Example 4, while stirring and warming gently, to produce a total of 100 g of solution.

Example B: 1% strength ointment for topical application:

1 g of the compound from Example 4 is ground with 5 g of viscous liquid paraffin. Thereafter, sufficient ointment base consisting of liquid paraffin and polyethylene is added to produce a total of 100 g of ointment.

Example C: 10% strength suspension elixir for oral administration:

Sufficient vegetable oil is added to a mixture of 10 g of the active compound from Example 1 and 0.05 g of sodium saccharin and 2 g of colloidal silica and 0.2 g of peppermint oil to produce a total of 100 g of suspension elixir.

Example D: Tablets, each containing 200 mg of active compound, for oral administration:

2 g of compound from Example 4, 1 g of lactose and 0.3 g of maize starch are granulated with 0.1 g of maize starch paste. The mixture is beaten through a sieve of about 4 to 6 mm mesh width and dried. This dried mixture is homogenized through a sieve of 0.8 to 1 mm mesh width and then mixed with 0.15 g of starch and 0.02 g of magnesium stearate. The mixture thus obtained is pressed to give 10 tablets.

The following non-limitative examples more particularly illustrate the active compounds of the present invention:

EXAMPLE 1

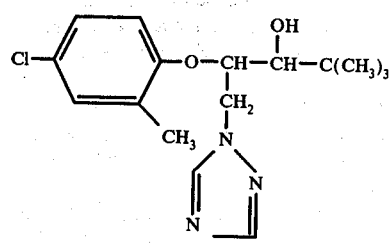

9.65 g (0.03 mol) of 1-(1,2,4-triazol-1-yl)-2-(methyl-4-chlorophenoxy)-4,4-dimethyl-pentan-3-one are dissolved in 100 ml of methanol and 2 g (0.05 mol) of sodium borohydride are added thereto in portions at 5° to 10° C. After stirring for 15 hours at room temperature, 10 ml of concentrated hydrochloric acid are added and the resulting suspension is stirred into 250 ml of saturated sodium bicarbonate solution. The resulting precipitate is filtered off, rinsed with 50 ml of water and dried.

9.1 g (94% of theory) of 1-(1,2,4-triazol-1-yl)-2-(2-methyl-4-chlorophenoxy)-3-hydroxy-4,4-dimethyl-pentane of melting point 124° to 126° C are obtained.

The starting compound is prepared as follows:

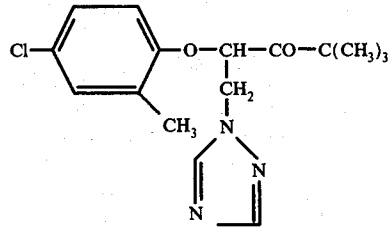

283 g (2 mols) of 4-chloro-2-methylphenol, 300 g of potassium carbonate and 2 g of potassium iodide are suspended in 2 l of anhydrous acetone and the mixture is heated to the boil. 359 g (2 mols) of bromopinacolone are then gradually added dropwise while stirring and the reaction mixture is heated for 5 hours under reflux. Thereafter, first the solvent and then the ketone are distilled off under reduced pressure. 381 g (79% of theory) of 1-(2-methyl-4-chlorophenoxy)-3,3-dimethyl-butan-2-one of boiling point 109°–112° C/ 0.1 mm are obtained.

144 ml (1.1 mols) of 30% strength formaldehyde solution and 8 ml of 10% strength aqueous sodium hydroxide solution are added to 145 g (0.6 mol) of 1-(4-chloro-2-methylphenoxy)-3,3-dimethyl-butan-2-one which have been dissolved in 400 ml of ethanol, and the reaction mixture is heated to the boil under reflux for 4 hours. The resulting solution is freed from the solvent under reduced pressure and the oily residue is taken up in 300 ml of ether and extracted with three times 200 ml of water. The organic phase is dried over sodium sulphate, filtered and distilled in vacuo.

After the solvent has passed over, 106 g (65% of theory) of 1-hydroxy-2-(1-methyl-4-chlorophenoxy)-4,4-dimethylpentan-3-one of boiling point 122° to 132° C/0.1 mm are obtained.

50 g (0.42 mol) of thionyl chloride are slowly added dropwise at room temperature to a solution of 106 g (0.39 mol) of 1-hydroxy-2-(2-methyl-4-chlorophenoxy)-4,4-dimethyl-pentan-3-one in 400 ml of methylene chloride while stirring and using reflux cooling, and the mixture is stirred overnight at room temperature. It is then distilled under reduced pressure.

93 g (82% of theory) of 1-chloro-2-(2-methyl-4-chlorophenoxy)-4,4-dimethyl-pentan-3-one of boiling point 113 to 117° C/0.2 mm are obtained.

43.4 g (0.15 mol) of 1-chloro-2-(2-methyl-4-chlorophenoxy)-4,4-dimethyl-pentan-3-one and 21.4 g (0.15 mol) of potassium carbonate are suspended in 300 ml of anhydrous acetone and 20.7 g (0.3 mol) of traizole are added dropwise thereto at the boil, while stirring. After boiling under reflux for 20 hours, the precipitate is filtered off, well rinsed with ether and discarded. The filtrate is freed from the solvent in vacuo and the oily residue is dissolved in 300 ml of ether and extracted twice with 200 ml of water to remove the excess triazole. The organic phase is dried over sodium sulphate, filtered and freed from the solvent in vacuo. The residue crystallizes after trituration with pentane.

30 g (62% of theory) of 1-(1,2,4-triazol-1-yl)-2-(2-methyl-4-chlorophenoxy)-4,4-dimethyl-pentan-3-one of melting point of 63° to 65° C are obtained.

EXAMPLE 2

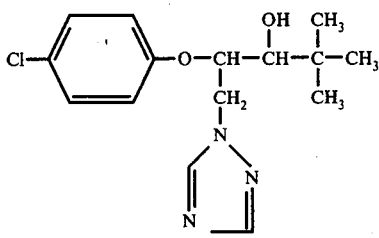

6.2 g (0.02 mol) of 2-(4'-chlorophenoxy)-1-(1,2,4-triazole-1-yl)-4,4-dimethyl-pentan-3-one are dissolved in 60 ml of ethanol and a sodium hydroxide solution containing 1.6 g (0.04 mol) of sodium hydroxide in 8 ml of water is added thereto, followed by 6.5 g (0.06 mol) of formamidinesulphonic acid. The reaction mixture is heated to the boil for 3 hours under reflux and filtered, and the solvent is distilled off in vacuo.

The oily residue is taken up in 50 mol of water and extracted with twice 50 ml of methylene chloride. The combined organic phases are washed with twice 50 ml of water, dried over sodium sulphate and freed from the solvent in vacuo.

The resulting oil is boiled up with petroleum ether, whereupon it crystallizes. Filtration gives 5 g (80% of theory) of 2-(4'-chlorophenoxy)-1-(1,2,4-triazol-1-yl)-4,4-dimethylpentan-3-ol of melting point 103° C.

EXAMPLE 3

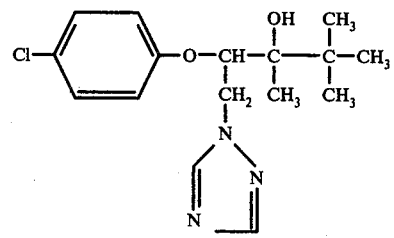

A solution of 31.2 g (0.22 mol) of methyl iodide in 100 ml of anhydrous ether is added dropwise to a suspension of 5.35 g (0.22 mol) of magnesium filings in 50 ml of anhydrous ether, while stirring and using reflux cooling; during the addition the solvent comes to the boil. After completion of the addition, a solution of 30.8 g (0.1 mol) of 2-(4'-chlorophenoxy)-1-(1,2,4-triazol-1-yl)-4,4-dimethylpentan-3-one in 100 ml of anhydrous ether is added dropwise to the Grignard solution obtained, and the mixture is heated to the boil for 18 hours, using reflux cooling.

After it has cooled, the reaction mixture is introduced into a solution of 80 g of ammonium chloride in 600 ml of water, 250 ml of ethyl acetate are added thereto and the mixture is stirred for 15 minutes. The organic phase is separated off and the aqueous phase is again extracted with ethyl acetate. The two ethyl acetate extracts are washed with twice 100 ml of water, dried over sodium sulphate and freed from the solvent in vacuo. The crystalline precipitate is taken up in hot petroleum ether, which leaves it undissolved, and is filtered off hot.

25 g (77% of theory) of 2-(4'-chlorophenoxy)-1-(1,2,4-triazol-1-yl)-3,4,4-trimethyl-pentan-3-ol of melting point 150° C are obtained.

The compounds of Examples 4 through 16 are set forth in Table 1 and prepared in analogous manner to that set forth above with respect to Examples 1, 2 and 3.

Table 1

Compounds of the formula:

$$R^1O-CH(CH_2-N\text{-triazole})-C(OH)(R^2)-R^3$$

| Example No. | R¹ | R² | R³ | Melting point, °C | Prepared by Method |
|---|---|---|---|---|---|
| 4 | 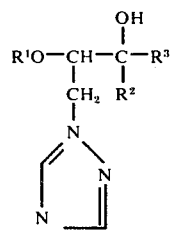 | H | C(CH₃)₃ | 106–108 | (c) |

Table 1-continued
Compounds of the formula:
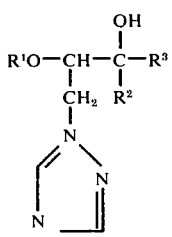
| Example No. | R¹ | R² | R³ | Melting point, °C | Prepared by Method |
|---|---|---|---|---|---|
| 5 | 3-Cl-C₆H₄ | H | C(CH₃)₃ | 131–133 | (c) |
| 6 | 2,4-Cl₂-C₆H₃ | H | C(CH₃)₃ | 115 | (c) |
| 7 | 2,4-Cl₂-C₆H₃ | H | C(CH₃)₃ | 165–167 | (c) |
| 8 | 2,3-(CH₃)₂-C₆H₃ | H | C(CH₃)₃ | 132–134 | (c) |
| 9 | 4-F-C₆H₄ | H | C(CH₃)₃ | 121–122 | (c) |
| 10 | C₆H₅ | H | C(CH₃)₃ | 129 | (c) |
| 11 | 4-F-C₆H₄ | CH₃ | C(CH₃)₃ | 160–164 | (e) |
| 12 | 4-F-C₆H₄ | —CH₂-C₅H₄N | C(CH₃)₃ | 152–155 | (e) |
| 13 | C₆H₅ | | C₆H₅ | H | 118–119 | (c) |
| 14 | 4-Cl-C₆H₄ | | C₆H₅ | H | 94–98 | (c) |
| 15 | 4-Cl-C₆H₄ | | 4-Cl-C₆H₄ | H | 134–135 | (c) |

Table 1-continued

Compounds of the formula:

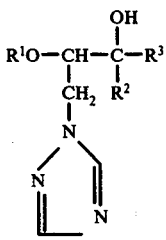

| Example No. | R¹ | R² | R³ | Melting point, °C | Prepared by Method |
|---|---|---|---|---|---|
| 16 | (3,4-dichlorophenyl) | (4-chlorophenyl) | H | 132–135 | (c) |

What is claimed is:

1. A pharmaceutical composition useful for treating mycotic infections in humans and animals which comprises an anti-mycotically effective amount of a compound of the formula $$R^1O-CH(CH_2-N\text{-imidazole})-C(OH)(R^2)-R^3$$

or a pharmaceutically acceptable non-toxic salt thereof wherein
R¹ is phenyl or naphthyl unsubstituted or substituted by 1 to 3 substituents selected from the group consisting of alkyl of 1 to 4 carbon atoms, halogen, haloalkyl of 1 or 2 carbon atoms in the alkyl moiety and 2 to 5 halo moieties, and phenyl;
R² is hydrogen; alkyl of 1 to 6 carbon atoms; or alkenyl of 2 to 6 carbon atoms; and
R³ is hydrogen or alkyl of 1 to 4 carbon atoms;
provided that when R³ is hydrogen, R² cannot be hydrogen; in combination with a pharmaceutically acceptable non-toxic inert diluent or carrier.

2. A pharmaceutical composition according to claim 1 wherein
R¹ is phenyl, naphthyl or phenyl substituted by 1 to 3 substituents selected from the group consisting of fluorine, chlorine, bromine, methyl, tert.-butyl, and phenyl;
R² is hydrogen or alkyl of 1 to 4 carbon atoms; and
R³ is hydrogen or alkyl of 1 to 4 carbon atoms;
provided that when R³ is hydrogen, R² cannot be hydrogen.

3. A pharmaceutical composition according to claim 1 wherein
R¹ is phenyl unsubstituted or substituted by 1 or 2 substituents selected from the group consisting of chlorine, fluorine, bromine and methyl;
R² is hydrogen or alkyl of 1 to 4 carbon atoms; and
R³ is alkyl of 1 to 4 carbon atoms.

4. A pharmaceutical composition according to claim 1 wherein
R¹ is phenyl, chlorophenyl, dichlorophenyl, fluorophenyl, bromophenyl or chloromethylphenyl;
R² is hydrogen, methyl or t.-butyl; and
R³ is t.-butyl.

5. A pharmaceutical composition according to claim 1 wherein
R¹ is 4-chlorophenyl or 4-fluorophenyl;
R² is hydrogen or methyl; and
R³ is t.-butyl; the hydrochloride salt thereof or the nitrate thereof.

6. A pharmaceutical composition according to claim 1 wherein
R¹ is phenyl unsubstituted or substituted by 1 or 2 members selected from the group consisting of chlorine, fluorine and methyl;
R² is hydrogen, methyl, cyclohexyl or benzyl; and
R³ is hydrogen or t.-butyl; provided that when R³ is hydrogen, R² cannot be hydrogen.

7. A pharmaceutical composition according to claim 1 wherein
R¹ is phenyl, chlorophenyl, dichlorophenyl, fluorophenyl, dimethylphenyl or chloromethylphenyl;
R² is hydrogen, methyl, phenyl, chlorophenyl, or benzyl; and
R³ is hydrogen or t.-butyl; provided that when R³ is hydrogen, R² cannot be hydrogen.

8. A pharmaceutical composition according to claim 1 wherein the compound is

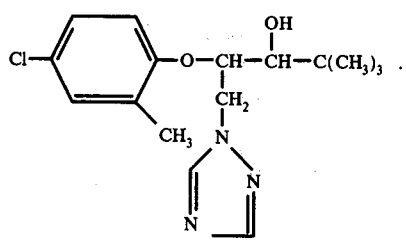

9. A pharmaceutical composition according to claim 1 wherein the compound is

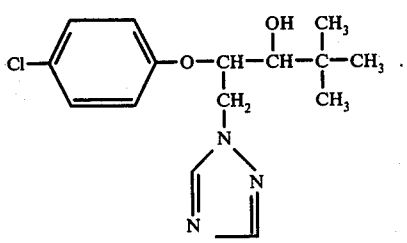

10. A pharmaceutical composition according to claim 1 wherein the compound is

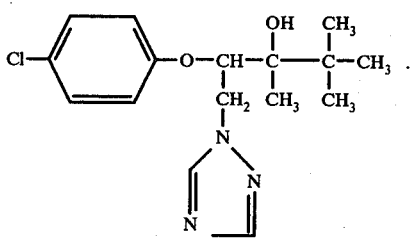

11. A pharmaceutical composition according to claim 1 wherein

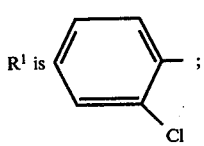

$R^2$ is hydrogen; and
$R^3$ is $C(CH_3)_3$.

12. A pharmaceutical composition according to claim 1 wherein

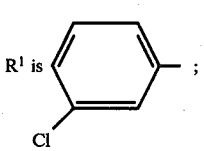

$R^2$ is hydrogen; and
$R^3$ is $C(CH_3)_3$.

13. A pharmaceutical composition according to claim 1 wherein

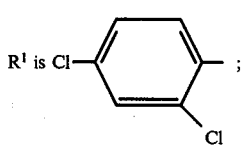

$R^2$ is hydrogen; and
$R^3$ is $C(CH_3)_3$.

14. A pharmaceutical composition according to claim 1 wherein

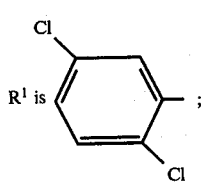

$R^2$ is hydrogen; and
$R^3$ is $C(CH_3)_3$.

15. A pharmaceutical composition according to claim 1 wherein

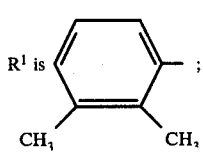

$R^2$ is hydrogen; and
$R^3$ is $C(CH_3)_3$.

16. A pharmaceutical composition according to claim 1 wherein

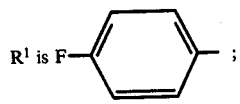

$R^2$ is hydrogen; and
$R^3$ is $C(CH_3)_3$.

17. A pharmaceutical composition according to claim 1 wherein

$R^2$ is hydrogen; and
$R^3$ is $C(CH_3)_3$.

18. A pharmaceutical composition according to claim 1 wherein

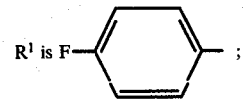

$R^2$ is $CH_3$; and
$R^3$ is $C(CH_3)_3$.

19. A pharmaceutical composition according to claim 1 in oral administration form.

20. A pharmaceutical composition according to claim 1 in topical application form.

21. A method for treating mycoses in humans and animals which comprises administering to said human or animal an antimycotically effective amount of a compound of the formula

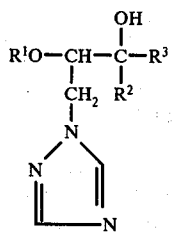

or a pharmaceutically acceptable non-toxic salt thereof wherein
$R^1$ is phenyl or naphthyl unsubstituted or substituted by 1 to 3 substituents selected from the group consisting of alkyl of 1 to 4 carbon atoms, halogen, haloalkyl of 1 or 2 carbon atoms in the alkyl moiety and 2 to 5 halo moieties, and phenyl;
$R^2$ is hydrogen; alkyl of 1 to 6 carbon atoms; or alkenyl of 2 to 6 carbon atoms; and
$R^3$ is hydrogen or alkyl of 1 to 4 carbon atoms; provided that when $R^3$ is hydrogen, $R^2$ cannot be hydrogen.

22. A method according to claim 21 wherein
$R^1$ is phenyl, naphthyl or phenyl substituted by 1 to 3 substituents selected from the group consisting of fluorine, chlorine, bromine, methyl, tert.-butyl, and phenyl;
$R^2$ is hydrogen or alkyl of 1 to 4 carbon atoms; and
$R^3$ is hydrogen or alkyl of 1 to 4 carbon atoms;

provided that when R³ is hydrogen, R² cannot be hydrogen.

23. A method according to claim 21 wherein
R¹ is phenyl unsubstituted or substituted by 1 or 2 substituents selected from the group consisting of chlorine, fluorine, bromine and methyl;
R² is hydrogen or alkyl of 1 to 4 carbon atoms; and
R³ is alkyl of 1 to 4 carbon atoms.

24. A method according to claim 21 wherein
R¹ is phenyl, chlorophenyl, dichlorophenyl, fluorophenyl, bromophenyl or chloromethylphenyl;
R² is hydrogen, methyl or t.-butyl; and
R³ is t.-butyl.

25. A method according to claim 21 wherein
R¹ is 4-chlorophenyl or 4-fluorophenyl;
R² is hydrogen or methyl; and
R³ is t.-butyl; the hydrochloride salt thereof or the nitrate thereof.

26. A method according to claim 21 wherein
R¹ is phenyl unsubstituted or substituted by 1 or 2 members selected from the group consisting of chlorine, fluorine and methyl;
R² is hydrogen, methyl, cyclohexyl or benzyl; and
R³ is hydrogen or t.-butyl;
provided that when R³ is hydrogen, R² cannot be hydrogen.

27. A method according to claim 21 wherein
R¹ is phenyl, chlorophenyl, dichlorophenyl, fluorophenyl, or chloromethylphenyl;
R² is hydrogen, methyl, phenyl, chlorophenyl, or benzyl; and
R³ is hydrogen or t.-butyl;
provided that when R³ is hydrogen, R² cannot be hydrogen.

28. A method according to claim 21 wherein
R¹ is phenyl, chlorophenyl, dichlorophenyl, fluorophenyl, dimethylphenyl or chloromethylphenyl;
R² is hydrogen, methyl, phenyl, chlorophenyl, or benzyl; and
R³ is hydrogen or t.-butyl;
provided that when R³ is hydrogen, R² cannot be hydrogen.

29. A method according to claim 21 wherein the compound is

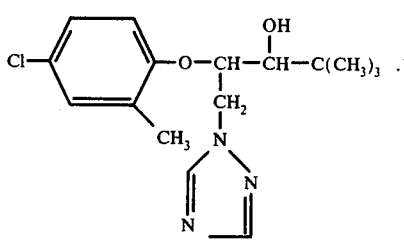

30. A method according to claim 21 wherein the compound is

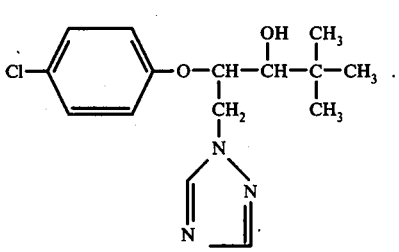

31. A method according to claim 21 wherein the compound is

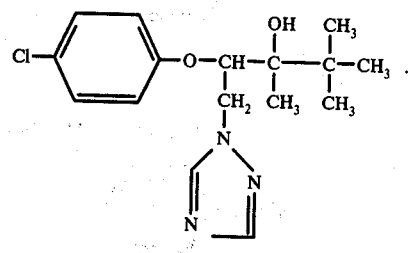

32. A method according to claim 21 wherein

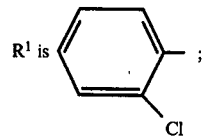

R² is hydrogen; and
R³ is C(CH₃)₃.

33. A method according to claim 21 wherein

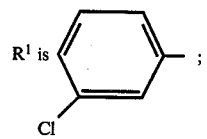

R² is hydrogen; and
R³ is C(CH₃)₃.

34. A method according to claim 21 wherein

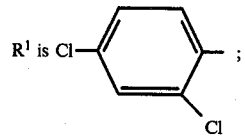

R² is hydrogen; and
R³ is C(CH₃)₃.

35. A method according to claim 21 wherein

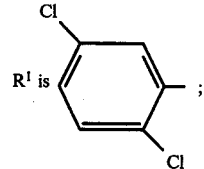

R² is hydrogen; and
R³ is C(CH₃)₃.

36. A method according to claim 21 wherein

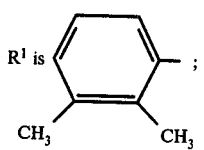

R² is hydrogen; and
R³ is C(CH₃)₃.

37. A method according to claim 21 wherein

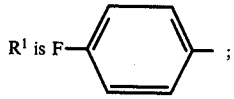

R² is hydrogen; and
R³ is C(CH₃)₃.

38. A method according to claim 21 wherein $R^1$ is 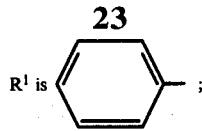

$R^2$ is hydrogen; and
$R^3$ is $C(CH_3)_3$.

39. A method according to claim 21 wherein $R^1$ is 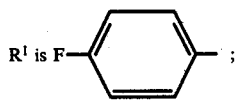

$R^2$ is $CH_3$; and
$R^3$ is $C(CH_3)_3$.

40. A method according to claim 21 wherein the administration is oral.

41. A method according to claim 21 wherein the administration is by topical application.

42. A method according to claim 21 wherein the antimycotically effective amount is from 10 mg/kg to 300 mg/kg per day.

43. A method according to claim 21 wherein the antimycotically effective amount is from 50 mg/kg to 200 mg/kg per day.

* * * * *